United States Patent [19]

Rosenberg et al.

[11] Patent Number: 5,432,196

[45] Date of Patent: Jul. 11, 1995

[54] PREPARATION OF AN ACTIVE SUBSTANCE SOLUTION WHICH CAN BE STERILIZED BY FILTRATION

[75] Inventors: Joerg Rosenberg, Ellerstadt; Rolf Neidhardt, Schwetzingen; Guenter Blaich, Weinheim, all of Germany

[73] Assignee: Knoll AG, Ludwigshafen, Germany

[21] Appl. No.: 182,087

[22] PCT Filed: Jul. 11, 1992

[86] PCT No.: PCT/EP92/01577

§ 371 Date: Jan. 13, 1994

§ 102(e) Date: Jan. 13, 1994

[87] PCT Pub. No.: WO93/01811

PCT Pub. Date: Feb. 4, 1993

[30] Foreign Application Priority Data

Jul. 22, 1991 [DE] Germany ................ 41 24 252.1

[51] Int. Cl.⁶ ............................................. A61K 31/275
[52] U.S. Cl. ...................................... 514/523; 558/390
[58] Field of Search ......................... 558/390; 514/523

[56] References Cited

U.S. PATENT DOCUMENTS

| | | | |
|---|---|---|---|
| 4,438,131 | 3/1984 | Ehrmann et al. | 424/278 |
| 4,777,183 | 10/1988 | Lenke et al. | 514/523 |
| 4,784,845 | 11/1988 | Desai et al. | 424/80 |
| 4,816,247 | 3/1989 | Desai et al. | 424/80 |
| 4,880,634 | 11/1989 | Speiser | 424/450 |
| 5,364,632 | 11/1994 | Benita et al. | 424/450 |

FOREIGN PATENT DOCUMENTS 456106 11/1991 European Pat. Off. .
2046094 11/1980 United Kingdom .

OTHER PUBLICATIONS

Actions of verapamil analogues, anipamil and . . . ; Curtis et al., Br. J. Pharmac. (1986), 88, pp. 355–361.

Primary Examiner—Joseph Paul Brust
Attorney, Agent, or Firm—Keil & Weinkauf

[57] ABSTRACT

A process for preparing an aqueous active substance solution which can be sterilized by filtration entails mixing anipamil hydrochloride with a phospholipid in the ratio of from 1:2 to 2:1 by weight, converting the resulting mixture into a gel by adding water at elevated temperature, and subsequently adding water to the gel at elevated temperature until the active substance is present in the required concentration.

1 Claim, No Drawings

PREPARATION OF AN ACTIVE SUBSTANCE SOLUTION WHICH CAN BE STERILIZED BY FILTRATION

Active substances for parenteral administration must be formulated as aqueous solutions. Considerable problems often arise from the sparing solubility of many active substances. In such cases it is frequently possible to prepare an appropriate solution only with the aid of cosolvents (eg. ethanol) and/or solubilizers.

One example of a sparingly soluble active substance is anipamil hydrochloride (EP 64 158) whose solubility in water is below 10 mg/liter.

Although it is generally easy to prepare aqueous solutions of sparingly soluble active substances with the aid of synthetic solubilizers, the latter substances are often unusable because of their side effects, especially after intravenous administration.

By contrast, naturally occurring phospholipids are known to be tolerated virtually without reaction even after parenteral administration, inter alia because they are normal components of every cell membrane. These "natural" solubilizers are likewise suitable for preparing solutions for injection and infusion of sparingly soluble active substances. For parenteral nutrition, for example, the sparingly soluble fats required are formulated with the aid of phospholipids (egg lecithin or soybean lecithin) as an emulsion which can be administered in relatively large amounts without the side effects observed with synthetic solubilizers. Emulsions of this type are composed of fat droplets which are finely dispersed in water. It is also possible for sparingly soluble active substances to be bound to the fat droplets in such emulsions and then administered parenterally in the form of such colloidal solutions.

Solutions containing phospholipids are in principle considerably more difficult to prepare than solutions containing synthetic solubilizers. On dispersion in water, phospholipids do not form clear micellar solutions like synthetic solubilizers, but always only form cloudy colloidal solutions with particles several $\mu m$ in size. Products containing such large particles cannot be administered parenterally because there is too great a risk of embolism. This is why, when phospholipids are used as solubilizers, a homogenization, eg. a high-pressure homogenization, must be carried out to reduce the particle size to below 1 $\mu m$. The expense of preparation is therefore distinctly higher when phospholipids are used as solubilizers because of the homogenization which is necessary.

We have now found a considerably simpler way to prepare anipamil-containing solutions.

The present invention relates to a process for preparing an aqueous anipamil solution which can be sterilized by filtration, which comprises mixing anipamil hydrochloride with a phospholipid in the ratio of from 1:2 to 2:1 by weight, converting the resulting mixture into a gel by adding water at elevated temperature while stirring, and subsequently adding water to the gel at elevated temperature until the active substance is present in the required concentration.

The process can be applied both to anipamil racemate and to the R and S enantiomers.

Suitable phospholipids are, inter alia, phosphatidylcholine, phosphatidylethanolamine, phosphatidylserine and phosphatidylglycerol, either alone or in combination with one another. Phosphatidylcholines are preferred, especially those which contain unsaturated fatty acid residues, such as oleic acid and/or linoleic acid residues. Highly purified egg and soybean lecithins which contain at least 80% phosphatidylcholine are particularly preferred. Anipamil hydrochloride and phospholipid are mixed in a ratio of from 1:2 to 2:1, preferably from 1:1.5 to 1.5:1, in particular of about 1:1. Water is then added stepwise, while stirring, to the active substance/phospholipid mixture at about 50°-90° C., preferably about 70°-80° C. The total amount of water added is about 20 ml per g of active substance/phospholipid mixture, adding 3-7 ml portions stepwise at intervals of 5-10 min. After formation of the gel it is necessary to dilute to the required concentration of active substance with more water at elevated temperature.

It is necessary for the process according to the invention that a) the phospholipid/anipamil mixture is hydrated stepwise and in small portions, and b) the hydration is carried out at elevated temperature. Satisfactory results are achieved, ie. the formation of colloidal solutions in which the particles are small and which can be sterilized by filtration, only when these two conditions are met, especially a). If, for example, the water is not added as indicated above (in portions) but too large an amount of water is added initially, the result is a cloudy colloidal solution which cannot be clarified even by prolonged stirring at elevated temperature. The particles in these solutions are then always distinctly above 1 $\mu m$ in size.

The phospholipid solutions are expediently rendered isotonic by adding a suitable physiologically tolerated substance. Examples of suitable substances are physiologically tolerated salts (NaCl) or non-ionic compounds such as sorbitol and, in particular, mono- or disaccharides such as sucrose. The sucrose is added as a solid when the anipamil/phospholipid mixture is being weighed out. It has emerged that in the presence of sucrose a gel was formed faster on hydration in a number of cases, so that it was unnecessary to expose the mixture to the elevated temperature for so long.

The process according to the invention results in colloidal solutions whose particles are, surprisingly, so small that sterilization by filtration is possible (0.2 $\mu m$ filter).

This result was surprising because, although a clear gel was formed on hydration in a similar experiment without anipamil hydrochloride, further dilution always resulted in colloidal solutions with particles several $\mu m$ in size. Only in the presence of the active substance is it possible to form colloidal phospholipid solutions with particle sizes which are otherwise achievable only by means of relatively elaborate homogenization processes.

The resulting solutions are very stable. The particle size distribution remains unchanged even after storage in a refrigerator for several months. No aggregation of the colloidal particles occurs. The solutions can also be diluted for infusions (for example with isotonic saline) without flocculation occurring. These diluted solutions are also stable on storage. The solutions are very well tolerated, especially on intravenous administration.

EXAMPLE 1

Anipamil-HCl/Lecithin Solution 11 mg/ml 1.10 g of anipamil hydrochloride monohydrate (1.91 mmol), 1.1 g of egg lecithin (lecithin E100 from Lipoid KG, Ludwigshafen) and 93.7 g of sucrose were weighed into a glass vessel which was heated to an internal temperature of 75° C. a waterbath thermostat. The hydration was then carried out with distilled water while stirring continuously, as shown below:

| Time (min) | Water added (ml) |
|---|---|
| 0 | 4 |
| 10 | 4 |
| 15 | 8 |
| 20 | 4 |

The mixture was stirred for a further 5 min at 75° C. after the last addition of water. The still hot solution was finally diluted to 100 ml with water in a volumetric flask.

The average size of the particles in the solution was 0.15–0.18 μm. The complete solution was sterilized by filtration and stored in a refrigerator at 5° C.

The resulting solution was stable at this temperature for at least 1 year. Before use, it is adjusted to the required concentration with physiological saline and can then be infused immediately.

Another possibility for the stabilization is to lyophilize the undiluted solutions by known processes.

EXAMPLE 2

Comparative Example

Preparation was carried out as in Example 1 but without the addition of anipamil-HCl. A very cloudy solution was obtained and this separated into two phases after only 30 min. The particles were above 1 μm in size, and sterilization by filtration was impossible.

EXAMPLE 3

Anipamil-HCl/Lecithin Solution 11 mg/ml

The experiment was carried out as in Example 1 but with only 0.7 g of egg lecithin (lecithin E100). The particles were, as in Example 1, about 0.15–0.18 μm in size, and sterilization by filtration was possible.

We claim:

1. A process for preparing an aqueous anipamil colloidal solution having a particle size of less than 0.2 μm, which comprises:
   a) mixing anipamil hydrochloride with a phospholipid selected from the group consisting of phosphatidylcholine, phosphatidylethanolamine, phosphatidylserine and phosphatidylglycerol, either alone or in combination, in a ratio of anipamil hydrochloride/phospholipid ratio of from 1:2 to 2:1 by weight; then
   b) adding water in a stepwise manner to the anipamil/phospholipid mixture at a temperature of between about 50° and 90° C. until a gel is formed; and then
   c) adding water to said gel at a temperature of between about 50° and 90° C.

* * * * *